United States Patent [19]

Endelson

[11] 4,327,755
[45] May 4, 1982

[54] DENTAL FLOSS DISPENSER IN CREDIT CARD FORMAT

[76] Inventor: Robert A. Endelson, 330 E. 79th St., New York, N.Y. 10021

[21] Appl. No.: 202,734

[22] Filed: Oct. 31, 1980

[51] Int. Cl.³ .............................................. A61C 15/00
[52] U.S. Cl. .................................. 132/92 R; 206/63.5; 206/388
[58] Field of Search ....................... 132/92 R, 91, 92 A, 132/93, 90; D28/64; 206/63.3, 63.5, 388, 417

[56] References Cited

U.S. PATENT DOCUMENTS

| | | | |
|---|---|---|---|
| D. 255,388 | 6/1980 | Olson | D28/64 |
| 817,050 | 4/1906 | De La Cour | 132/92 R |
| 2,083,398 | 6/1937 | Rohland | 132/91 |
| 2,446,383 | 8/1948 | Motz | 206/388 |
| 2,451,849 | 10/1948 | Massimiana | 132/92 R |
| 2,510,194 | 6/1950 | Thomas | 132/92 R |
| 3,280,971 | 10/1966 | Regan, Jr. | 206/63.3 |
| 3,869,044 | 3/1975 | Olsson et al. | 206/388 |
| 3,918,466 | 11/1975 | Peebles, Jr. | 132/91 |
| 4,162,688 | 7/1979 | Tarrson et al. | 132/92 |

FOREIGN PATENT DOCUMENTS 705213 6/1931 France ............................... 132/92 R

*Primary Examiner*—Gene Mancene
*Assistant Examiner*—John J. Wilson
*Attorney, Agent, or Firm*—Michael Ebert

[57] ABSTRACT

A dental floss dispenser in a credit card format permitting the dispenser to be conveniently carried in a wallet. The dispenser comprises a base panel having a peripheral ridge to define a shallow well within which is nested a supply of dental floss in flattened coil form. The leading end of the coil passes out of the well through an aperture and is caught by a lug adjacent an edge notch cut in the base panel. Anchored in the well is a blade whose cutting edge is exposed by the notch, whereby when floss is pulled out of the well to provide a usable length, the trailing end thereof may be cut by the blade. The dispenser is completed by a face panel bonded to the ridge to encapsulate the floss supply, the face panel having a corresponding notch.

10 Claims, 9 Drawing Figures

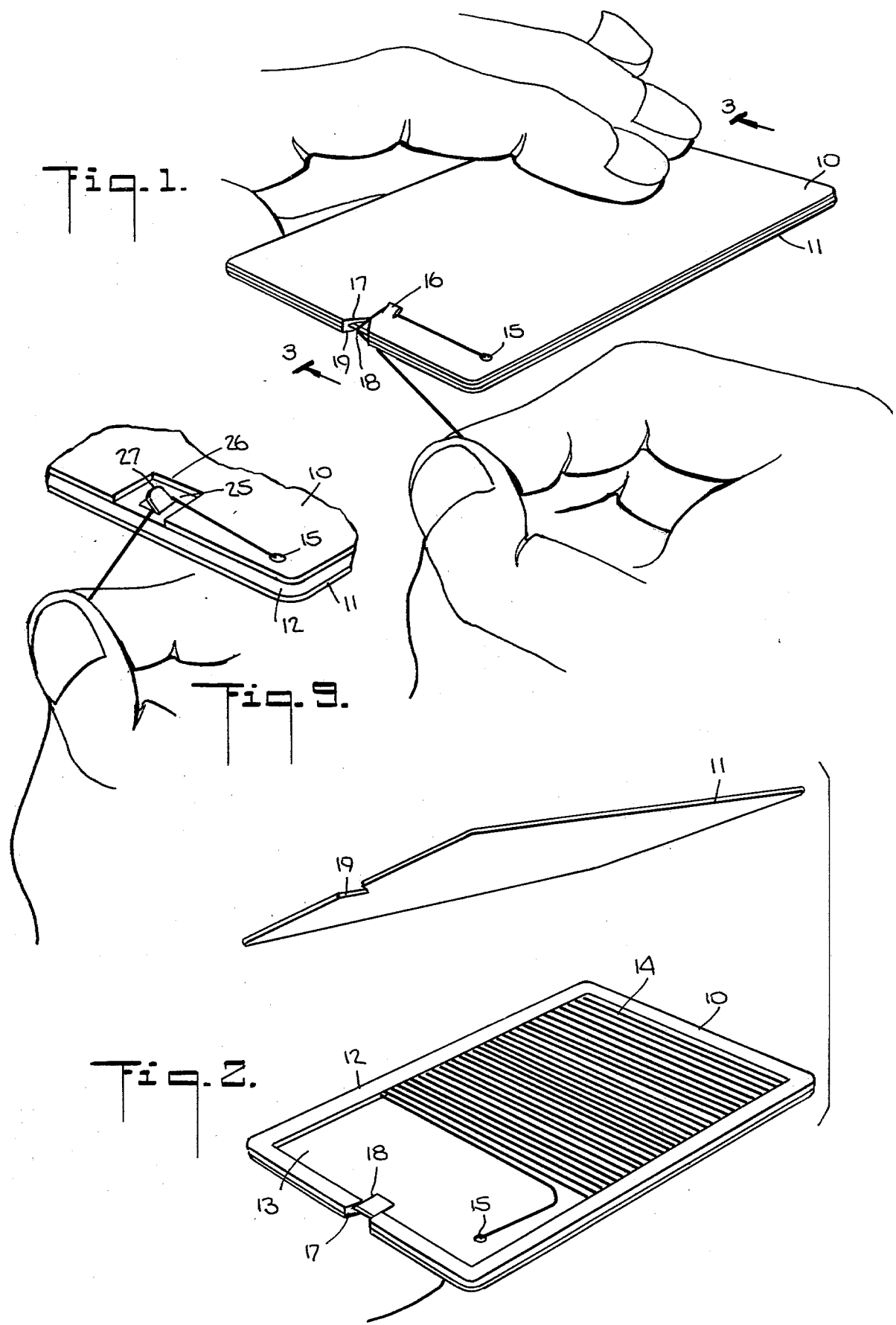

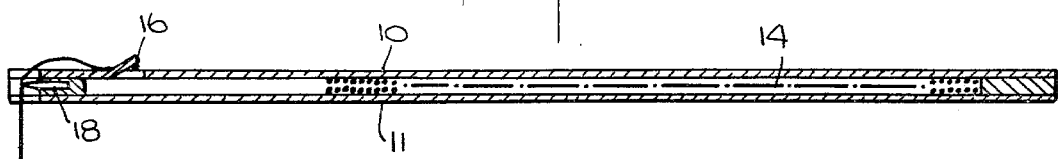
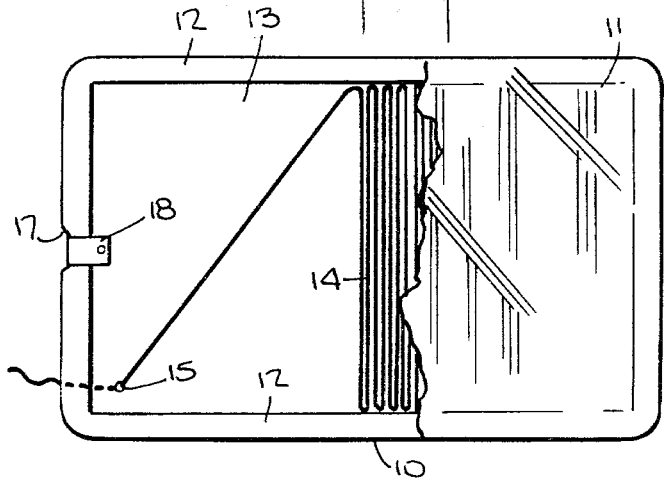
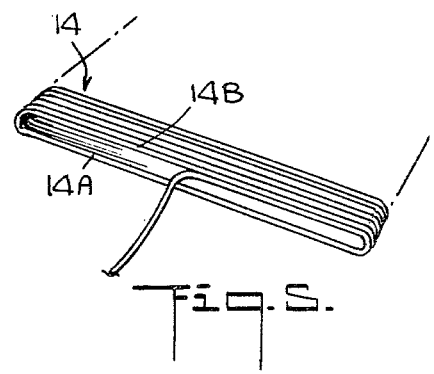
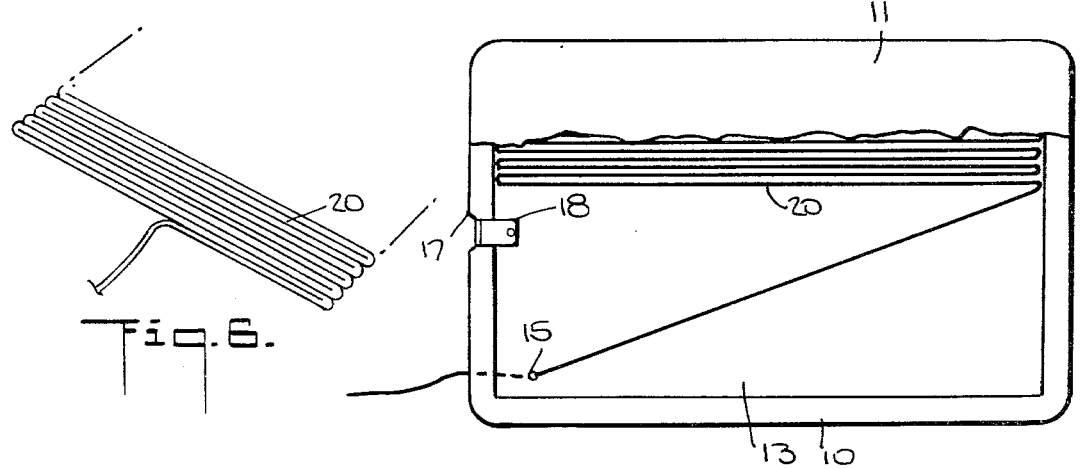
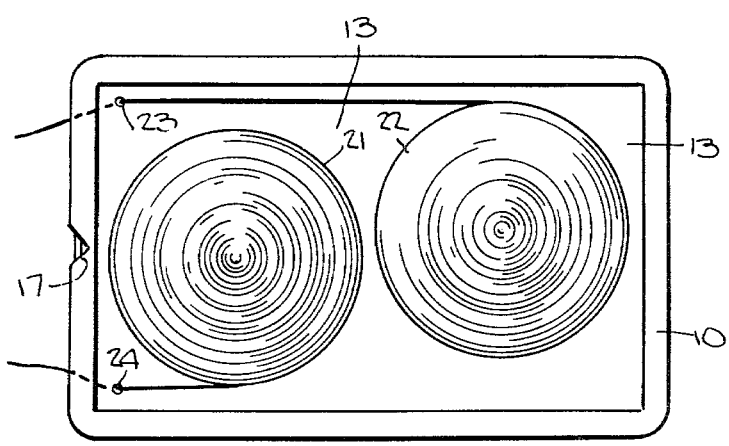

DENTAL FLOSS DISPENSER IN CREDIT CARD FORMAT

BACKGROUND OF INVENTION

This invention relates generally to dental floss dispensers, and more particularly to a highly compact dispenser in a credit card format, making it feasible to conveniently carry the dispenser in a wallet or elsewhere on the person.

In large measure, dental disease is due to the accumulation of bacterial plaque on the teeth and gums. This plaque acts to generate acids which attack the teeth and gums, giving rise to tooth decay and caries, and resulting in periodontal disease. The therapeutic value of dental floss to dislodge debris collected between the teeth and to break up colonies of bacteria that gather near the gum line is well established.

Dental floss generally takes the form of a nylon or cotton string or other suitable filament of synthetic or natural fibers. Usually, the floss is waxed so that as the floss is extruded through a space between the teeth, its passage is lubricated. The advantage of dental floss is that it can traverse hard-to-reach places between the teeth and under bridges that are otherwise inaccessible to toothbrushes or other dental appliances. While toothpicks are sometimes used rather than dental floss, picks tend to impact debris between the teeth rather than to dislodge the debris.

Good dental hygiene requires the use of floss after every meal so that food particles lodging between the teeth are not permitted to remain in these sites. Since the typical dental floss container or dispenser cannot be conveniently carried on the person, it is not as a practical matter possible for most individuals to follow the dictates of good dental practice. Thus while these dispensers may be stored in household bathroom cabinets, an individual who wishes to apply dental floss away from home is faced with the problem of how best to carry a floss container in an inconspicuous manner.

Commercially-available dental floss dispensers are generally of the type disclosed in the Tarrson U.S. Pat. No. 4,162,688. This dispenser includes a box-like container having a reel of dental floss therein which is payed out through a top opening, the container being provided with a cutting blade so that a suitable length of dental floss may be separated from the supply. Because of the three-dimensional bulk of this boxlike dispenser, it cannot be conveniently carried in a clothing pocket or elsewhere on the person.

A somewhat more compact dental floss dispenser is illustrated in the Wells U.S. Pat. No. 3,930,059, in which the floss is wound on a spool rotatably mounted within a wafer-like housing whose outlet is provided with a cutting knife. However, this type of dispenser is not sufficiently compact to be inserted in a wallet or billfold. Other types of dental floss dispensers or holders are disclosed in the Peebles, Jr. U.S. Pat. No. 3,918,466; the Strock U.S. Pat. No. 4,211,330 and the Rohland U.S. Pat. No. 2,083,398.

SUMMARY OF INVENTION

In view of the foregoing, the chief object of this invention is to overcome the practical drawbacks of existing types of dental floss dispensers by providing a dispenser in a credit card format, making it feasible to carry the dispenser in a wallet or billfold, or even in a shirt pocket without discomfort and without injury to the dispenser.

Because credit cards are currently in widespread use, most commercial wallets incorporate flat jackets or pockets adapted to accommodate credit cards without causing the wallet to bulge. Hence a dental floss dispenser in accordance with the invention may be stored inconspicuously in a wallet and put to use away from home under circumstances where dental floss is usually not available.

More particularly, an object of this invention is to provide a dental floss dispenser in a credit card format not much thicker than a standrd credit card yet large enough to encapsulate a substantial supply of dental floss. Thus while the dispenser is essentially planar and highly compact, the supply therein is not quickly exhausted and it may be put to use repeatedly.

Also an object of the invention is to provide a disposable dental floss dispenser that may be mass-produced at low cost, the dispenser encapsulating a floss supply to maintain the floss in sterile condition.

Yet another object of the invention is to provide a dental floss dispenser with a transparent face panel to expose the floss supply whereby the extent of depletion is apparent to the user.

A significant advantage of dental floss dispensers in accordance with the invention is that they may be personalized and printed under computer control with the names of individuals derived from the computer memory and with the title of an advertiser, very much in the manner of existing credit cards, whereby such printed dispensers may be distributed as advertising premiums that are likely to be treasured by recipients. Or such printed dental floss dispensers may be given away by restaurants and other establishments rather than match books, for there is diminishing interest in the latter because of the prevalence of disposable butane lighters.

Briefly stated, these objects are attained in a dental floss dispenser in credit card format permitting the dispenser to be conveniently stored in a wallet or elsewhere on the person. The dispenser comprises a base panel having a peripheral ridge to define a shallow well within which is nested a supply of dental floss in flattened coil form.

The leading end of the coil passes out of the well through a corner aperture and is caught in a lug adjacent an edge notch cut in the base panel. Anchored in the well is a blade whose cutting edge is exposed by the notch, whereby when floss is pulled out of the well to an extent providing a usable length, the trailing end thereof may be cut by the blade. The dispenser is completed by a face panel bonded to the ridge of this base to encapsulate the floss supply, the face panel having a corresponding notch.

OUTLINE OF DRAWINGS

For a better understanding of the invention as well as other objects and further features thereof, reference is made to the following detailed description to be read in conjunction with the accompanying drawings, wherein:

FIG. 1 is a perspective view of a first embodiment of a dental floss dispenser in a credit card format in accordance with the invention, the dispenser being held by the user in one hand, while a length of dental floss pulled out of the dispenser is cut by the other hand;

FIG. 2 is an exploded view of the dispenser;

FIG. 3 is a longitudinal section taken through the plane indicated by line 3—3 in FIG. 1;

FIG. 4 is a plan view of the dispenser;

FIG. 5 is a separate perspective view of the flattened helical-coil floss supply;

FIG. 6 is a separate perspective view of an alternative form of dental floss supply;

FIG. 7 is a plan view of a second embodiment of a dental floss dispenser in accordance with the invention;

FIG. 8 is a plan view of a third embodiment of a dispenser in accordance with the invention; and FIG. 9 is an alternative form of a floss-cutting blade.

DESCRIPTION OF INVENTION

First Embodiment

Referring now to FIGS. 1 to 5, there is shown a dental floss dispenser in accordance with the invention in a credit card format, the dispenser including a rectangular base panel 10 and a complementary face panel 11 superposed thereon. Both panels are preferably fabricated of flexible synthetic plastic material such as polyvinyl chloride or other thermoplastic material. Typical credit card dimensions may be used for the panels, such as 3⅜ inches by 2⅛ inches.

Base panel 10 is provided with a peripheral ridge 12 to define a shallow rectangular well 13. Within the well is nested a supply of dental floss in the form of a flattened helical coil 14 of waxed dental floss, the supply being shown separately in FIG. 5. In practice, the ridge and base panel may be molded in one piece. The preferred technique for fabricating the flattened helical coil is to wind the dental floss on a thin metal plate or mandrel whose dimensions are close to those of well 13. The flattened coil is then pressed with a heated iron which acts to set and sinter the wax constituent of the floss whereby when the mandrel is withdrawn, the unsupported flattened coil retains it shape and may be easily placed within well 13.

Flattened coil 14, as shown in FIG. 5, is made up of a lower course 14A and an upper course 14B; hence the depth of well 13, as determined by the height of ridge 12, must be sufficient to accommodate both courses.

the leading end of coil 14 is threaded through an aperture 15 in the well adjacent one corner of the base panel to pass out of the dispenser. The leading end, as best seen in FIG. 1, is caught in a lug 16 struck out of base panel 10 at the rear thereof. Because the base panel is of flexible plastic material, the lug is somewhat resilient and acts as a holding catch for the floss.

Lug 16 is adjacent a triangular edge notch 17 cut at the midpoint of one edge of base panel 10. Anchored in well 13 is a small metal blade 18 which overlies the apex of notch 17 so that its cutting edge is exposed thereby. The dispenser is completed by marginally bonding face panel 11 to ridge 12 of the base panel, face panel 11 having a notch 19 therein corresponding to notch 17. This bonding may be done by a suitable adhesive or by heat and pressure to effect thermal bonding of the thermoplastic panels.

When face panel 11 is bonded to base panel 10 to complete the structure of the dispenser, flattened coil 14 is encapsulated therein and is thereby sealed to maintain its sterile condition. In practice, face panel 11 may be made of transparent material to reveal the underlying coil and show the extent to which it is depleted. The base panel is preferably of opaque plastic material which may be printed or embossed to carry identification, advertising or promotional material, as previously explained. And just as it is a matter of prestige in certain circles to own a gold toothpick, the panels may be of gold-pigmented plastic to create a prestige floss dispenser.

To use the dispenser, one merely pulls out an appropriate length of floss, the trailing end of which is then cut by blade 18 in the manner shown in FIG. 1. The dispenser is held in one hand while the floss is manipulated by the other.

Other Embodiments

The embodiment of the dental floss dispenser shown in FIGS. 6 and 7 is identical to that in FIG. 1, save that in this instance the dental floss supply is not a flattened helix but is a coil formed by a single serpentine layer, each course of which runs the length of well 13.

Because of this single layer arrangement, it is possible to make the dispenser even thinner than the first embodiment. In all other respects, this dispenser functions in the same manner of the first dispenser.

In the third embodiment shown in FIG. 8, instead of a single flattened coil serving as a dental floss supply, two spiral coils 21 and 22 are provided, the leading ends of these coils passing out of respective corner apertures 23 and 24. While this arrangement does not fully utilize the capacity of well 13, it is of advantage where high speed machinery is available for forming spiral coils without the need for a mandrel as in the helical coil of FIG. 5.

Rather than a lug to catch the floss and a separate cutting blade, the blade may be of the dual-function type shown by plate 25 in FIG. 9, where a rectangular notch 26 exposes the plate whose bent-out lug 27 acts both as a catch and as a cutting edge at the junction between the plate and the lug.

While there have been shown and described preferred embodiments of a dental floss dispenser in credit card format in accordance with the invention, it will be appreciated that many changes and modifications may be made therein without, however, departing from the essential spirit thereof. Thus instead of a dental floss supply in the form of a flat helical coil, use may be made of a rectangular swatch of dental floss, the swatch being knitted or otherwise fabricated by textile machinery so that it can be unravelled by pulling out the leading end of the floss. The term "flattened coil" as used herein, is intended to cover a switch supply of this type.

And instead of printing on the base panel, it may be preferable to print on the face panel, even if it is transparent; for the base panel is embossed or molded, whereas the face panel may be derived from a continuous web of film material. This web may first be printed on a web press and then severed into individual face panel sections.

Another useful application for a printed dental floss dispenser in credit card form is as an appointment reminder to be given out by dentists. The present practice in dental offices, after a visit, is to give the patient a card having written thereon the date and time of his appointment. Such cards are often mislaid or discarded by patients. But a patient whose appointment card is also a dental floss dispenser is likely to retain the card and to consult it each time he extracts a piece of floss therefrom.

I claim:

1. A thin flat dental floss dispenser in a credit card format, said dispenser comprising:

A. a rectangular base panel provided with a peripheral ridge to define a shallow well, said panel having a well aperture therein and an edge notch;

B. a flattened unsupported supply coil of dental floss nested in the well, and having a thickness substantially equal to the depth of the well, the leading end of the coil passing out of the aperture;

C. a blade adjacent said notch and anchored in said well, said blade having a cutting edge exposed by said notch, and D. matching face panel marginally bonded to said ridge to encapsulate said coil, said base panel and said face panel having a combined thickness and rectangular dimensions similar to those of a typical credit card whereby the dispenser may be conveniently stored in a wallet or otherwise inconspicuously carried on a person.

2. A dispenser as set forth in claim 1, further including a lug stuck out of said base panel to catch said leading end.

3. A dispenser as set forth in claim 1, wherein said blade is a plate having a lug bent out therefrom to form both a cutting edge and a catch for the floss.

4. A dispenser as set forth in claim 1, wherein said coil is a flattened helix formed of waxed dental floss.

5. A dispenser as set forth in claim 1, wherein said face panel is of transparent material to reveal the supply coil.

6. A dispenser as set forth in claim 1, wherein said panels are both formed of flexible thermoplastic material.

7. A dispenser as set forth in claim 1, wherein the outer surface of said face panel is printed.

8. A dispenser as set forth in claim 1, wherein said flattened coil is a serpentine configuration of dental floss.

9. A dispenser as set forth in claim 1, wherein said flattened coil is in a spiral formation.

10. A dispenser as set forth in claim 1, wherein one of said panels has printed thereon an appointment form for use by dentists to indicate the time and date of the next appointment, whereby when the card is given to a patient, he is reminded of his next appointment each time he makes use of the dental floss dispenser.

* * * * *